United States Patent
Jarvik (12)

(10) Patent No.: US 6,344,022 B1
(45) Date of Patent: Feb. 5, 2002

(54) RIGHT VENTRICULAR BYPASS DEVICES AND METHODS OF THEIR USE DURING HEART SURGERY

(76) Inventor: Robert Jarvik, 333 W. 52nd St., New York, NY (US) 10019

( * ) Notice: Subject to any disclaimer, the term of this patent is extended or adjusted under 35 U.S.C. 154(b) by 0 days.

(21) Appl. No.: 09/356,446

(22) Filed: Jul. 19, 1999

(51) Int. Cl.[7] .................................................. A61M 1/10
(52) U.S. Cl. .......................... 600/16; 623/3.16; 623/3.1
(58) Field of Search ............................. 600/16; 623/2.1, 623/910, 3.1, 3.16

(56) References Cited

U.S. PATENT DOCUMENTS

| | | | |
|---|---|---|---|
| 4,008,710 A | 2/1977 | Chmiel | 600/16 |
| 5,743,845 A | 4/1998 | Runge | 600/16 |
| 5,984,956 A | 11/1999 | Tweden et al. | 623/1 |
| 6,090,140 A | 7/2000 | Gabbay | 623/2.1 |
| 6,139,487 A | 10/2000 | Siess | 600/16 |

Primary Examiner—Carl Layno

(57) ABSTRACT

During coronary artery bypass grafting (CABG) surgery in cases when cardio-pulmonary bypass is not used, at times when the heart is manipulated or lifted the inflow to the right ventricle may be kinked and obstructed. Then flow across the lungs will decrease and left ventricular filling may output will be diminished. To avoid this problem a passive shunt, which in the preferred embodiment is a valved shunt, is used to conduct blood from the inferior vena cava (IVC) via the right atrium to the pulmonary artery (PA) bypassing the right ventricle. The shunt uses large diameter cannulae to keep its resistance low. The valve prevents blood from flowing from the PA into the IVC. The shunt may also use a manually actuated shutoff valve or may have a portion which can be clamped. During surgery, the patient may be fluid loaded so that the right atrial pressure is high, such as 25 mmHg. Then, with the shunt open, if the right ventricular inflow becomes obstructed during manipulation of the heart, blood will flow passively across the shunt and across the lungs. The shunt may also be used with a left ventricular bypass pump during CABG surgery.

11 Claims, 3 Drawing Sheets

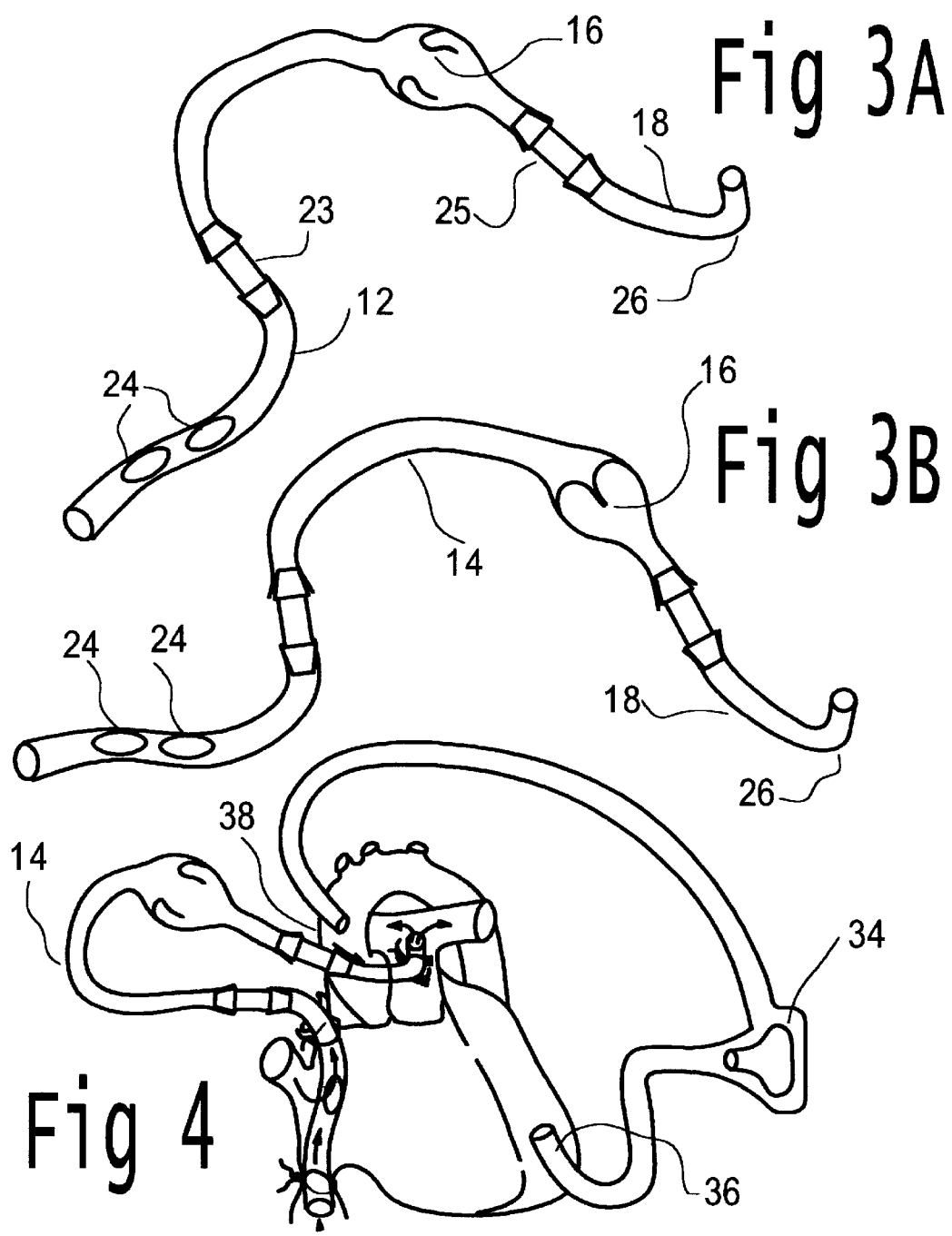

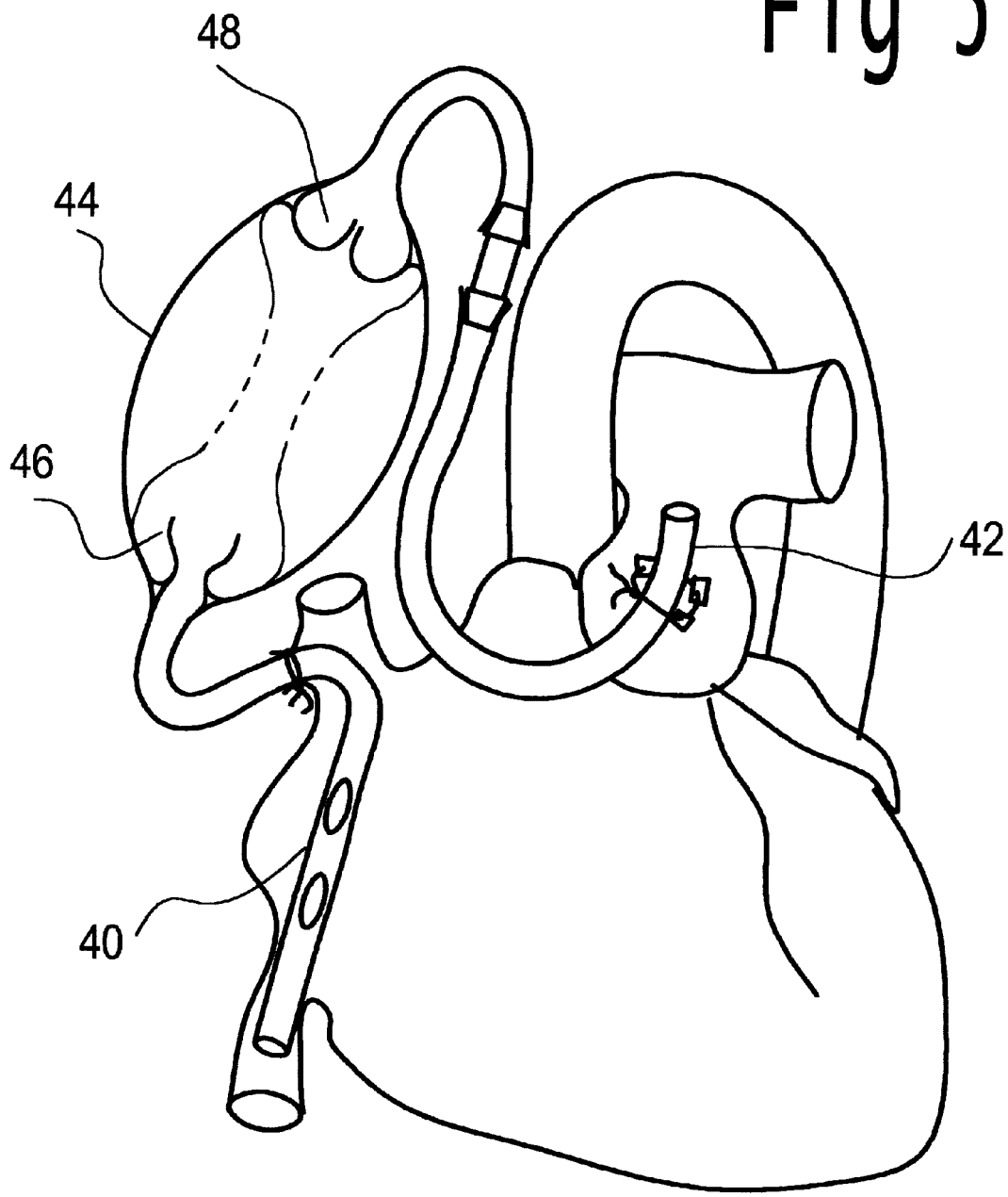

RIGHT VENTRICULAR BYPASS DEVICES AND METHODS OF THEIR USE DURING HEART SURGERY

BACKGROUND OF THE INVENTION

Surgery for grafting of the coronary arteries has most commonly been done using cardiopulmonary bypass with the heart stopped. Recently, the advantages of avoiding the blood damage caused by the heart lung machine have been recognized, and a number of methods to operate on the coronary arteries without using oxygenators have become more common. The patient's natural heart or some type of heart assist device is used to pump the blood through the body and through the lungs. In some operations, particularly when the heart must be lifted or displaced to gain access to the site of a coronary artery graft anastomosis, the flow through the heart may be diminished due to kinking of the atria or blood vessels directly adjacent to the heart.

In the case of kinking of the inflow to the right side of the heart, blood flow across the lungs will be diminished, which in turn will diminish filling of the left side of the heart which will decrease cardiac output.

The present invention provides a very simple and inexpensive device and method to maintain the cardiac output even while the inflow to the right side of the heart is kinked or obstructed by compression. A passive shunt from the right heart inflow to the pulmonary artery is created which is opened during the time when the natural right inflow is blocked. The preferred embodiment includes an inflow cannula and a pulmonary artery cannula, and a tube connecting them containing a flow actuated valve to prevent back flow from the pulmonary artery. A portion of the tube is adapted to be clamped to shut off the flow completely. The preferred placement is with the inflow cannula in the inferior vena cava and the outflow cannula in the pulmonary artery. The inflow cannula may include side holes adapted to permit blood from the right atrium (originating from the SVC and coronary sinus) to also enter it.

During use, the shunt is placed and either clamped or left so that pressure from the pulmonary artery closes the valve. The patient is then given a sufficient volume of fluid so that his/her right atrial pressure is elevated [above normal] to about 25 mmHg. When the heart is manipulated during surgery and the right inflow is obstructed, the clamp is removed and blood will flow passively through the shunt to bypass the obstruction. This will maintain sufficient blood across the lungs to supply the left heart and maintain the patient's arterial blood pressure.

Alternative embodiments of the shunt include a model with no valve, in which case the surgeon must attend to clamping and un-clamping the shunt as necessary, and another embodiment having two valves and a compressible chamber between them, adapted to be squeezed manually to provide a hand actuated right heart bypass pump.

OBJECTS OF THE INENTION

It is an object of the present invention to provide a device to bypass the right heart during surgical manipulation.

It is a further object of the invention to provide a valved right heart bypass shunt adapted to prevent back flow from the pulmonary artery when the right ventricle is receiving sufficient filling to pump effectively, and automatically act as a shunt when the right heart filling is obstructed.

It is another object of the invention to provide a method to permit surgical manipulation of the heart using a passive right heart bypass shunt.

It is a still further object of the invention to provide a simple, inexpensive right heart bypass pump which is manually actuated by the surgeon during brief periods of use while the natural heart is surgically manipulated.

It is another object of the invention to provide a passive right heart shunt which may be used in conjunction with a left heart assist device so as to maintain the pulmonary circulation even at times when the right heart inflow is obstructed.

BRIEF DESCRIPTION OF THE SEVERAL VIEWS OF THE DRAWINGS

FIG. 3A is a line drawing of a similar embodiment of the invention to the one shown in shown in FIG. 2. In this embodiment, a flexing polymer leaflet valve is used, and the leaflets are shown open.

FIG. 3B is a line drawing of a similar embodiment of the invention to the one shown in shown in FIG. 1. In this embodiment, a flexing polymer leaflet valve is used, and the leaflets are shown closed.

FIG. 4 is a diagram of a patient's heart during surgery in which a device of the present invention is used for passive right heart bypass and a centrifugal pump is used for left heart bypass pumping.

FIG. 5 is a drawing of an embodiment of the invention including a resilient tube which may be squeezed by hand to effect pumping. Dotted lines indicate the tube in a position after it has been squeezed to eject blood.

SPECIFIC DESCRIPTION OF THE INVENTION

Figure 1:
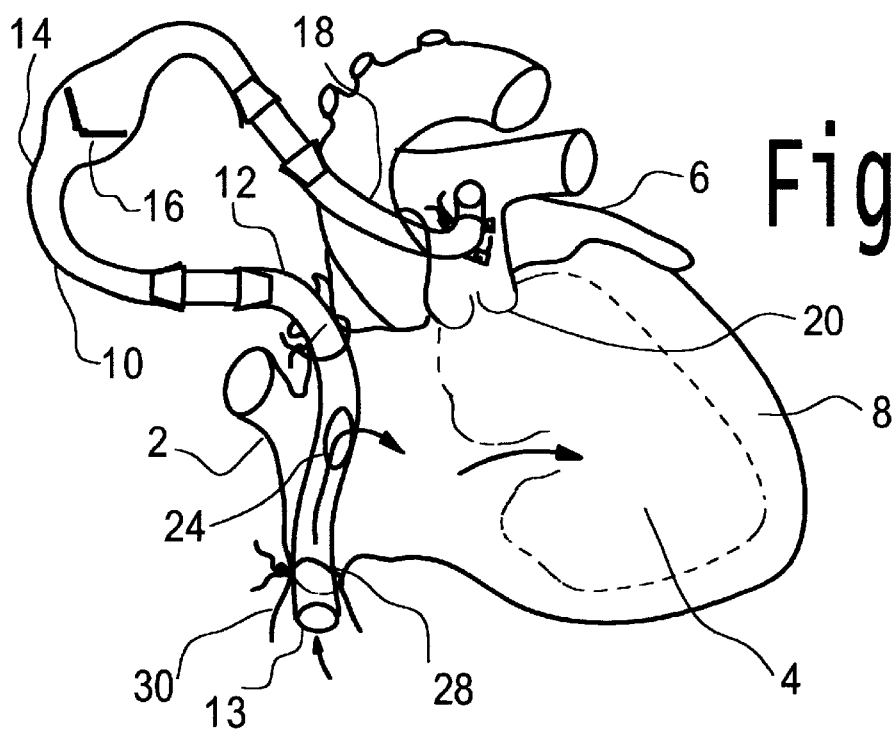
FIG. 1 is a line drawing representing a patient's heart at the time of surgery with a valved right heart bypass device in place. The illustration shows a pivoting leaflet valve which is closed. The inferior vena cava is ligated. Arrows indicate blood flow passing from the inferior vena cava, through part of the device, and into the natural right ventricle.

In its most simple form, the present invention constitutes a flexible tube having one end adapted for cannulation of the vena cava and the other end adapted for cannulation of the pulmonary artery. In practice, a single tube is sub-optimal because during cannulation air must be vented. Therefore, two tubes and a connector are preferable. The device may be assembled from components commonly utilized for cardiopulmonary bypass if no internal valve is included. FIG. 1 shows one highly simplified embodiment. The heart includes the right atrium 2, the right ventricle 4, the left atrium 6, and the left ventricle 8. The shunt 10, includes an inflow cannula 12 passed through the right atrium with its tip 13 located in the inferior vena cava. The shunt includes a flexible conduit 14 within which a valve 16, is contained. The conduit is in turn connected to a pulmonary artery cannula 18 with its tip placed in the pulmonary artery 20. The valve 16 is adapted to close when the pressure on the pulmonary artery side is higher then the pressure on the right atrial side.

Figure 2:
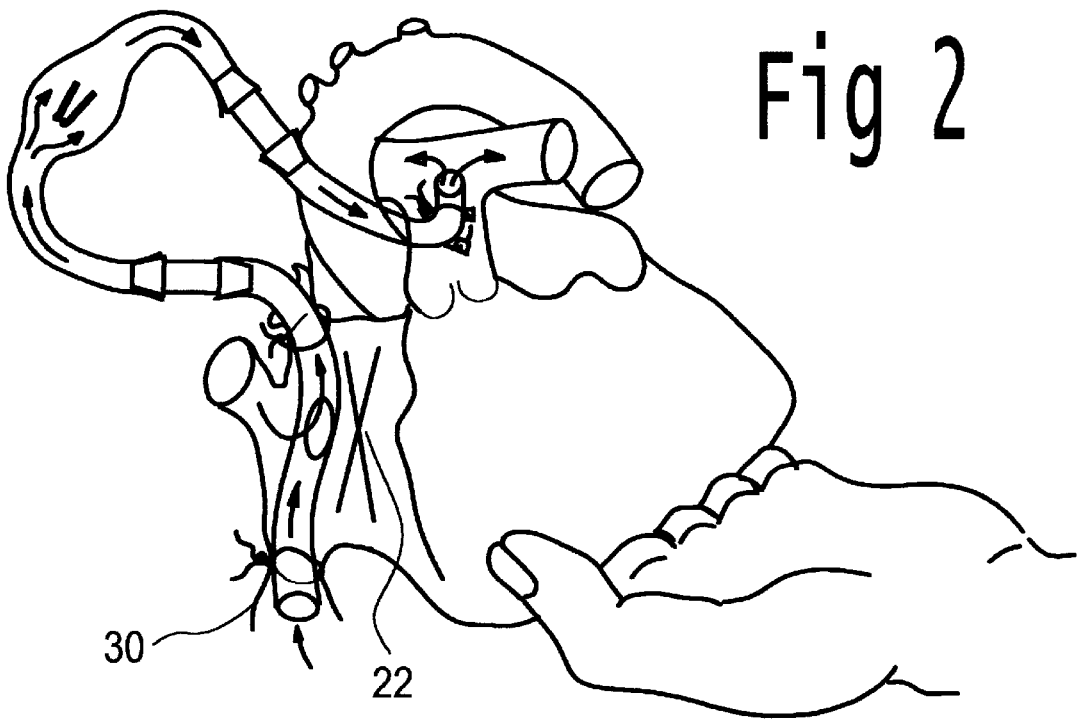
FIG. 2 is a line drawing representing the heart with a right bypass device in place while the heart is manipulated by the surgeon's hand. The arrows in the figure indicate the direction of blood flow through the device.

During surgery when manipulation of the heart causes obstruction of the flow of blood into the right ventricle (indicated at 22 by the X in FIG. 2) the valve 16 opens and blood flows across the shunt as shown by the arrows in FIG. 2. When the obstruction is not present, as in FIG. 1, blood flows through the right heart normally.

The prefered embodiment of the valved shunt is shown in FIG. 3A which illustrates the situation with inflow to the right ventricle obstructed so that the blood flow passes through the shunt. Two barbed connectors, 23 and 25 are provided to attach the two cannula and flexible conduit together, and to permit air venting during surgical placement. As best seen in FIGS. 1 & 2, the inflow cannula 12 includes side holes 24 located so that they are positioned within the right atrium during use. The valve 16 and the is preferably a simple monocusp or bicusp polymer valve. The outflow cannula—includes a curvature 26 near the point of entry into the pulmonary artery to permit positioning out of the way of surgical access to the heart. When the inflow cannula is placed it is retained and sealed with a umbilical tapes at the right atrium 28, and also around the inferior vena cava, 30. Blood flows into the cannula from the IVC through its tip 13, and from the right atrium via the side holes 24. When the inflow to the right atrium is not obstructed, as shown in FIG. 3B, the blood from the inferior vena cava flows into the inflow cannula tip and then out through the side holes, permitting it to enter the right ventricle across the tricuspid valve 32.

FIG. 4 shows the device together with a left ventricular bypass pump 34 placed between the left ventricular apex 36, and the aorta 38. When used as shown, in conjunction with the left assist pump, the shunt and pump together permit the full cardiac output of the patient to be pumped by the assist pump even when the inflow to the right ventricle is obstructed. This permits the heart to be slowed down with drugs such as Esmolol which stills its motion and simplifies coronary artery suturing. It also permits complete arrest of the heart with cold cardioplegia.

FIG. 5 shows a shunt configured to permit temporary pumping by manual massage. The device includes an inflow cannula 40 and an outflow cannula 42, between which is placed a valved pumping chamber 44. This chamber includes an inflow valve 46, and an outflow valve 48. The wall of the chamber is constructed of a blood compatible material, preferably an elastomer or other polymer. The chamber may be a rather soft walled tube of approximately 50–100 cc volume, or may be a bulb like structure which returns to its full position after being squeezed, like the bulb of a bulb syringe. In use, during periods of time when the surgeon needs to increase the flow into the pulmonary artery, the chamber wall is alternately squeezed and relaxed to actuate it as a pump. Since the period of time while the right ventricular inflow is obstructed by manipulating the heart is usually only about 10–20 minutes, it is practical for the surgeon to manually squeeze the pump at a rate of 30–50 times per minute, which can pump 2–4 L/min of blood at a pressure of about 25–35 mmHg. This can be accomplished without undue fatigue because the pressure in the pulmonary artery is low. Using a manual pump on the left side would also be possible, but since the aortic pressure is higher, its use would be more tiring for the individual squeezing it.

The information disclosed in the description of the present invention is intended to be representative of the principles I have described. For example, Various commonly applied methods of canulation and combinations of access sites may be used without departing from the scope of the present invention. Cannulation may be via the inferior vena cava, superior vena cava, right atrial wall, right atrial appendage, right ventricule, main pulmonary artery trunk or via a large branch of the pulmonary artery. A number of commonly applied cannulation techniques may be used including but not limited to fixation of the cannulae in place with ligatures, umbilical tapes, or purse string sutures. It will thus be seen that the objects of the invention set forth above and those made apparent from the preceding description are efficiently obtained and that certain changes may be made in the above articles and constructions without departing from the scope of the invention. It is intended that all matter contained in the above description and shown in the accompanying drawings shall be interpreted as illustrative but not in a limiting sense.

It is also understood that the following claims are intended to cover all of the generic and specific features of the invention herein described and all statements of the scope of the invention which, as a matter of language, might be said to fall there between.

What is claimed is:

1. A passive right atrium to pulmonary artery shunt, for use during coronary artery bypass surgery comprising;
    a. A venous uptake cannula to remove blood from the inferior vena cave, superior vena cava, or right atrium, or from any combination of those vascular structures,
    b. A second cannula to introduce blood into the pulmonary artery, and,
    c. Means to connect said venous uptake cannula to said pulmonary artery cannula.

2. The passive shunt of claim 1 further including a tube interconnecting said inflow cannula and said pulmonary artery cannula having a portion of said tube adapted to be clamped by the surgeon.

3. The passive shunt of claim 1 further including valve means to permit flow from said shunt into the pulmonary artery when said valve means are open and to prevent flow from the pulmonary artery into the shunt when said valve means are closed.

4. The passive shunt of claim 3 in which said valve means comprise a polymer valve.

5. The passive shunt of claim 3 in which said valve means comprise a pivoting leaflet or flow accuated valve.

6. The passive shunt of claim 1 in which said venous uptake cannula has one or more side holes positioned such that when said cannula is inserted across the right atrium and into the inferior vena cava, said side holes will reside within the right atrium.

7. A manually actuated right heart bypass pump comprising,
    a. A venous uptake cannula to remove blood from the inferior vena cave, superior vena cava, or right atrium, or from any combination of those vascular structures,
    b. A second cannula to introduce blood into the pulmonary artery,
    c. A manually compressible polymeric pumping chamber interposed between said venous uptake cannula to said pulmonary artery cannula including both inflow valve means and outflow valve means which permit blood to enter said chamber only from said venous uptake cannula means, and to exit said chamber only through said pulmonary artery cannula means.

8. The manually actuated right heart bypass pump of claim 7 in which said compressible pumping chamber is a soft walled tube.

9. The manually actuated right heart bypass pump of claim 7 in which said compressible pumping chamber includes resilient means to change its shape so as to increase the volume within it when it is manually released after having been manually compressed.

10. A method of sustaining adequate circulatory function during manipulation or retraction of the heart comprising,
    a. Creating an alternate path (shunt) for blood to flow around a portion of the anatomic structure conducting blood into the right ventricle which is susceptible to obstruction by kinking or compression during manipulation or surgical retraction of the heart,
    b. Increasing the right atrial blood pressure above normal, and,
    c. Occluding said shunt with clamping means or valve means during times when the inflow to the right ventricle is not obstructed.

11. The method of sustaining adequate circulatory function during manipulation or retraction of the heart of claim 10, in which said shunt includes manually actuated pumping means and said pumping means are employed during the period of time that the heart is manipulated or retracted.

* * * * *